(12) United States Patent
Wheeler et al.

(10) Patent No.: US 7,815,920 B2
(45) Date of Patent: Oct. 19, 2010

(54) METHOD OF PREPARING AN ANTIGEN-CONTAINING FORMULATION

(75) Inventors: Alan Wheeler, Horsham (GB); Anthony Berry, Horsham (GB)

(73) Assignee: Allergy Therapeutics (UK) Ltd, West Sussex (GB)

(*) Notice: Subject to any disclaimer, the term of this patent is extended or adjusted under 35 U.S.C. 154(b) by 50 days.

(21) Appl. No.: 10/211,388

(22) Filed: Aug. 2, 2002

(65) Prior Publication Data

US 2003/0007977 A1 Jan. 9, 2003

Related U.S. Application Data

(62) Division of application No. 09/399,217, filed on Sep. 17, 1999, now Pat. No. 6,440,426.

(30) Foreign Application Priority Data

Sep. 21, 1998 (GB) ................................ 9820525.5

(51) Int. Cl.
*A61K 39/00* (2006.01)
(52) U.S. Cl. ............... 424/278.1; 424/283.1; 424/184.1
(58) Field of Classification Search ................ 424/93.1, 424/184.1
See application file for complete search history.

(56) References Cited

U.S. PATENT DOCUMENTS

| | | | | |
|---|---|---|---|---|
| 3,541,201 A | * | 11/1970 | Brown | ........................ 424/490 |
| 3,792,159 A | | 2/1974 | Green et al. | |
| 4,070,455 A | | 1/1978 | Green et al. | |
| 4,258,029 A | | 3/1981 | Moloney et al. | |
| 4,912,094 A | | 3/1990 | Myers et al. | |
| 4,956,489 A | * | 9/1990 | Auriol et al. | ................... 560/40 |
| 4,987,237 A | | 1/1991 | Myers et al. | |
| 5,244,663 A | | 9/1993 | Bruttmann et al. | |
| 5,750,110 A | | 5/1998 | Prieels et al. | |
| 5,762,943 A | | 6/1998 | Dolovich et al. | |
| 5,776,468 A | | 7/1998 | Hauser et al. | |
| 5,795,862 A | | 8/1998 | Frank et al. | |
| 5,973,128 A | | 10/1999 | Lingwood et al. | |
| 5,997,873 A | | 12/1999 | Srivastava | |
| 6,146,632 A | | 11/2000 | Momin et al. | |
| 2003/0165512 A1 | | 9/2003 | Wheeler et al. | |
| 2005/0123570 A1 | | 6/2005 | Ulrich et al. | |

FOREIGN PATENT DOCUMENTS

| EP | 0239400 | 8/1994 |
|---|---|---|
| EP | 0640347 | 3/1995 |
| EP | 0182442 | 4/1996 |
| EP | 0988862 A3 | 6/2001 |
| EP | 1031347 B1 | 4/2002 |
| GB | 1128637 | 9/1968 |
| GB | 1377074 | 12/1974 |
| GB | 1492973 | 11/1977 |
| GB | 2220211 | 1/1990 |
| WO | WO 92/16556 | 10/1992 |
| WO | WO 94/27636 | 12/1994 |
| WO | WO 95/05850 | 3/1995 |
| WO | WO 95/17209 | 6/1995 |
| WO | WO 96/25664 A1 | 8/1996 |
| WO | WO 96/34626 | 11/1996 |
| WO | WO 98/43670 | 10/1998 |
| WO | WO 98/44947 | 10/1998 |
| WO | WO 98/58956 A3 | 12/1998 |
| WO | WO 99/10375 | 3/1999 |
| WO | WO 99/16884 | 4/1999 |
| WO | WO 99/24577 A1 | 5/1999 |
| WO | WO 99/64067 | 12/1999 |
| WO | WO 99/66043 | 12/1999 |
| WO | 00/29582 A3 | 5/2000 |
| WO | 00/50078 A1 | 8/2000 |
| WO | 00/62801 A3 | 10/2000 |
| WO | 00/65058 A1 | 11/2000 |
| WO | 00/72876 A3 | 12/2000 |
| WO | 00/78353 A3 | 12/2000 |
| WO | 01/29214 A1 | 4/2001 |
| WO | 01/51082 A1 | 7/2001 |

OTHER PUBLICATIONS

Stearyl Tyrosine information page.*
Cleland et al. Critical Reviews in Therp. Drug Carrier Systemes, 10(4):307-377, 1993.*
Holen et al. "Specific T cell lines for ovalbumin, ovomucoid, lysozyme and two OA synthetic epitopes, generated from egg allergic patients' PBMC," *Clin. Exp. Allerg.* (1996) 26:1080-1088, abstract.

(Continued)

*Primary Examiner*—Michael Szperka
*Assistant Examiner*—Yunsoo Kim
(74) *Attorney, Agent, or Firm*—Karen Canaan; CanaanLaw, P.C.

(57) ABSTRACT

An antigen-containing formulation is provided, comprising: (a) an antigen; (b) a TH1-inducing adjuvant; and (c) a sparingly soluble amino acid or a derivative thereof. The adjuvant may be, for example, monophosphoryl lipid A, 3'-de-O-acetylated monophosphoryl lipid A, derivatives thereof, or any other adjuvant that enhances an individual's TH1 response to the antigen. Suitable amino acids include tyrosine, tryptophan, derivatives thereof, and the like. Methods for using the formulation are also provided; in a particularly preferred embodiment, the formulation is used as a vaccine.

15 Claims, No Drawings

OTHER PUBLICATIONS

Hoyne et al., "Peptide-mediated regulation of the allergic immune response," Immunol. Cell Biol. (1996) 74:180-186.

Ngo et al. (1994), *The Protein Folding Problem and Tertiary Structure Prediction*, Mertz, Jr. et al. Eds., Birkhauser Boston, pp. 491-495.

Schneerson, et al., "Evaluation of monophosphoryl lipid A MPL as an adjuvant enhancement of the serum antibody response in mice to polysaccharide-protein conjugates by concurrent injection with MPL," J. Immunol. (1991) 147:2136-2140.

Ulrich and Myers, "Monophosphoryl Lipid A as an Adjuvant. Past Experiences and New Directions," Vaccine Design: The Subunit and Adjuvant Approach (Powell & Newman, eds., Plenum Press, N.Y. 1995).

Marsh, *Preparation and Properties of "Allergoids" Derived from Native Pollen by Mild Formalin Treatment*, Int. Arch. Allergy 41:199-215 (1971).

Allergy Therapeutics Pollinex Quattro® Brochure (1999).

Office Action for U.S. Appl. No. 11/040,952, dated Oct. 30, 2008, Double-Patenting Rejection.

Office Action for U.S. Appl. No. 11/040,952, dated Jul. 8, 2009, Double-Patenting Rejection.

Cox et al. (1997), "Adjuvants—A Classification and Review of Their Modes of Action," Vaccine 15(3):248-256.

Nixon-George et al. (1990), "The Adjuvant Effect of Stearyl Tyrosine on a Recombinant Subunit Hepatitis B Surface Antigen," *The Journal of Immunology* 144(12):4798-4802.

Penney et al. (1993), "Further Studies on the Adjuvanticity of Stearyl Tyrosine and Ester Analogues," Vaccine 11:1129-1134.

Sasaki et al. (1998), "Comparison of Intranasal and Intramuscular Immunization Against Human Immunodeficiency Virus Type 1 with a DNA-Monophosphoryl Lipid A Adjuvant Vaccine," Infection and Immunity 66(2):823-826.

Scalzo et al. (1995), "Induction of Protective Cytotoxic T Cells to Murine Cytomegalovirus by Using a Nonapeptide and a Human-Compatible Adjuvant," Journal of Virology 69(2):1306-1309.

Wheeler et al. (1982), "L-Tyrosine as an Immunological Adjuvant," *Int. Archs Allergy appl. Immun.* 69:113-119.

Ribi Adjuvant Fact Sheet (2003).

Akahira-Azuma et al., Early Delayed-Type Hypersensitivity Eosinophil Infiltrates Depend on T Helper 2 Cytokines and Interferon-Gamma via CXCR3 Chemokines, Immunology 111:306-317 (2004).

Chauncey et al., Enzymes of Human Saliva, The Determination, Distribution, and Origin of Whole Saliva Enzymes, J. Dental Res. 33(3):321-334 (1954).

Chauncey, Salivary Enzymes, J. Am. Dental Assoc. 63:42-50 (1961).

Dalton et al., The Solubilities of Certain Amino Acids in Water, the Densities of Their Solutions At Twenty-five Degrees, and The Calculated Heats of Solution and Partial Molal Volumes, J. Biol. Chem. 103(2):549-576 (1933).

Dearman et al., Divergent Antibody Isotype Responses Induced in Mice by Systemic Exposure to Proteins: a Comparison of Ovalbumin with Bovine Albumin, Food and Chemical Toxicology 38:351-360 (2000).

Dehlink et al., Absence of Systemic Immunologic Changes During Dose Build-up Phase and Early Maintenance Period in Effective Specific Sublingual Immunotherapy in Children, Clinical and Experimental Allergy 36:32-39 (2006).

Drachenberg et al., A Well-Tolerated Grass Pollen-Specific Allergy Vaccine Containing a Novel Adjuvant, Monophosphoryl Lipid A, Reduces Allergic Symptoms after only Four Preseasonal Injections, Allergy 498-505 (2001).

Drachenberg et al., Short-Term Immunotherapy with Tree Pollen Allergoids and the Adjuvant Monophosphoryl A—Results from a Multi-Centre, Placebo-Controlled Randomised, Double-Blind Study, Allergologie 25(9):466-474 (2002).

Drachenberg et al., Short-Term Immunotherapy Using an Allergy Vaccine Adjuvanted with Monophosphoryl Lipid A: A Post-Marketing Surveillance Study, Int. Rev. Allergol. Clin. Immunol. 8(4):219-223 (2002).

Drachenberg et al., Efficacy and Tolerability of Short-Term Specific Immunotherapy with Pollen Allergoids Adjuvanted by Monophosphoryl Lipid A (MPL) for Children and Adolescents, Allergol ET Immunopathol 31 (5):270-277 (2003).

Dunn et al., The Solubility of the Amino Acids in Water, J. Biol. Chem. 103(2):579-595 (1933).

Garren et al., Buccal Drug Absorption. I. Comparative Levels of Esterase and Peptidase Activities in Rat and Hamster Buccal and Intestinal Homogenates, Int'l J. Pharmaceutics 48:189-194 (1988).

Gonzalez-Hernandez et al., Peripheral Blood CD161+T Cells from Asthmatic Patients are Activated During Asthma Attack and Predominantly Produce IFN-Gamma Scand, J. Immunol. 65:368-375 (2007).

Hertl et al., Immunologic Mechanisms in Hypersensitivity Reactions to Metal Ions: an Overview, Allergy 55:108-115 (2000).

Jackson et al., Reduction of Human Anti-Tetanus Toxoid Antibody in hu-PBL-SCID mice by Immunodominant Peptides of Tetanus Toxoid, Clin Exp Immunol 137:245-252 (2004).

Johansen et al., Immunogenicity and Protective Efficacy of a Formalin-Inactivated Rotavirus Vaccine Combined with Lipid Adjuvants, Vaccine 21:368-375 (2003).

Lindquist et al., Esterases in Human Saliva, Enzyme, 20:277-291 (1975).

Lindquist et al., Origin of Esterases in Human Whole Saliva, Enzyme, 22:166-175 (1977).

Mamessier et al., Cytokines in Atopic Diseases: Revisiting the Th2 Dogma, Eur. J. Dermatol. 16(2):103-113 (2006).

Marsh et al., Studies on "Allergoids" Prepared from Naturally Occurring Allergens, Immunology 18:705-722 (1970).

McCluskie et al., CpG DNA is an Effective Oral Adjuvant to Protein Antigens in Mice, Vaccine 19:950-957 (2001).

Moran et al., Chemical Modification of Crude Timothy Grass Extract (III) the Effect of Glutaraldehyde Induced Aggregation of Antigenic and Immunogenic Properties, Int. Arch. Allergy Appl. Immunol. 55:315-321 (1977).

Pajno et al., Clinical and Immunologic Effects of Long-term Sublingual Immunotherapy in Asthmatic Children Sensitized to Mites: A Double-Blind, Placebo-Controlled Study, Allergy 55:842-849 (2000).

Patel et al., Pollinex Quattro: A Novel and Well-Tolerated, Ultra Short-Course Allergy Vaccine, Expert. Rev. Vaccines 5(5):617-629 (2006).

Patterson et al., Polymerized Ragweed Antigen E(I) Preparation and Immunological Studies, J. Immunol. 110:1402-1412 (1973).

Patterson et al., Polymerized Ragweed Antigen E(II) Preparation and Immunological Studies, J. Immunol. 110:1413-1418 (1973).

Patterson et al., Polymerized Ragweed Antigen E(III) Preparation and Immunological Studies, J. Immunol. 112:1855-1860 (1974).

SRI-RAM, Chemical Modification of Proteins and Their Significance in Enzymology, Immunochemistry, and Related Subjects, Advances in Enzymology: And Related Subjects of Biochemistry 24:105-160 (F.F. Nord, ed., John Wiley & Sons, 1962).

Stuck et al., Short-Term Preseasonal Immunotherapy with Birch Pollen Allergoid Plus Monophosphorylipid A (MPL): Influence on Cytokine Production of Peripheral T Cells in Patients with Allergic Rhinitis, Allergy Clin Immunol Int—J World Allergy Org 16(2):60-64 (2004).

Tan et al., Human Saliva Esterases: Genetic Studies, Hum. Heredity 26:207-216 (1976).

Valdez et al., Interactions of the Salivary and Gastronintestinal System I. The Role of Saliva in Digestion, Digestive Diseases 9(9):125-132 (1991).

Van Ginkel et al., Vaccines for Mucosal Immunity to Combat Emerging Diseases, Emerging Infectious Diseases, Emerging Infectious Diseases 6(2):123-132 (2000).

Verhoef et al., Transport of Peptide and Protein Drugs Across Biological Membranes, Eur J. Drug Met. Pharm. 15(2): 83-93 (1990).

Vogel et al., Drug Discovery and Evaluation, Pharmacological Assays pp. 440-444 (1996).

Voudras et al., Double-blind, Placebo-Controlled Evaluation of Sublingual Immunotherapy with Standardized Olive Pollen Extract in Pediatric Patients with Allergic Rhinoconjuntivitis and Mild Asthma Due to Olive Pollen Sensitization, Allergy 53:662-672 (1998).

Wheeler et al., Chemical Modification of Crude Timothy Grass Extract (II) Class and Specificity of Antibodies Induced by Chemically Modified Timothy Grass Pollen Extract, Int. Arch. Allergy Appl. Immunol. 50:709-728 (1976).

Wheeler et al., A Th1-Inducing Adjuvant, MPL®, Enhances Antibody Profiles in Experimental Animals Suggesting it has the Potential to Improve the Efficacy of Allergy Vaccines Int. Arch. Allergy Immunol. 126:135-139 (2001).

Yang et al., Mechanisms of Monophosphoryl Lipid A Augmentation of Host Responses to Recombinant HagB from Porphyromonas Gingivalis, Infection and Immunity 70(7):3557-3565 (2002).

Yssel et al., Regulatory T Cells and Allergic Asthma, Microbes and Infection (3) 899-904 (2001).

Zhou et al., Comparison of Enzyme Activities of Tissues Lining Portals of Absorption of Drugs Species Differences, Int'l J. Pharmaceutics 70(3):271-283 (1991)(Biosis Abstract).

* cited by examiner

METHOD OF PREPARING AN ANTIGEN-CONTAINING FORMULATION

CROSS-REFERENCE TO RELATED APPLICATIONS

This application is a divisional of U.S. Ser. No. 09/399,217, filed Sep. 17, 1999, now U.S. Pat. No. 6,440,426, which claimed priority under 35 U.S.C. §119 to U.K. Patent Application No. 9820525.5, filed Sep. 21, 1998.

TECHNICAL FIELD

The present invention relates to a novel formulation particularly, but not exclusively, for use in immunization.

BACKGROUND

The immune system has evolved specifically to detect and eliminate foreign or new material from a host. This material may be of viral, bacterial, or parasitic origin and may reside outside or within the cells of the host, or be of neoplastic origin.

The immune response to antigen is generally either cell mediated (T-cell mediated killing) or humoral (antibody production via recognition of whole antigen). The pattern of cytokine production by TH (T-Helper) cells involved in an immune response can influence which of these response types predominates: cell mediated immunity (TH1) is characterized by high IL-2 and IFNγ but low IL-4 production, whereas in humoral immunity (TH2) the pattern is low IL-2 and IFNγ but high IL-4, IL-5, IL-10. Since the secretory pattern is modulated at the level of the secondary lymphoid organ or cells, pharmacological manipulation of the specific TH cytokine pattern can influence the type and extent of the immune response generated.

The TH1-TH2 balance refers to the interconversion of the two different forms of helper T cells. The two forms have large scale and opposing effects on the immune system. If an immune response favors TH1 cells, then these cells will drive a cellular response, whereas TH2 cells will drive an antibody-dominated response. The type of antibodies responsible for some allergic reactions is induced by TH2 cells.

Vaccination is the best known and most successful application of immunological principles to human health. Naturally, to be introduced and approved, a vaccine must be effective and the efficacy of all vaccines is reviewed from time to time. Many factors affect vaccine efficacy. An effective vaccine must: induce the right sort of immunity; be stable on storage; and have sufficient immunogenicity. With non-living vaccines, in particular, it is often necessary to boost their immunogenicity with an adjuvant. This can also apply to some live, e.g., attenuated, vaccines. An "adjuvant" is a substance that enhances the immune response to an antigen.

During work in the 1920s on the production of animal antisera for human therapy, it was discovered that certain substances, notably aluminum salts, added to or emulsified with an antigen, greatly enhance antibody production, i.e., they act as adjuvants. Aluminum hydroxide is still widely used with, for example, diphtheria and tetanus toxoids.

GB-A-1 377 074, corresponding to U.S. Pat. No. 3,792,159, describes a process for preparing coprecipitates of tyrosine having an allergen dispersed therein.

GB-A-1 492 973, corresponding to U.S. Pat. No. 4,070,455, describes a process for preparing coprecipitates of tyrosine having a modified allergen dispersed therein. The allergen is modified by treatment with an agent, such as glutaraldehyde, which causes intra-molecular cross-linking and reduces the allergenicity of the product relative to the unmodified allergen.

3 De-O-acylated monophosphoryl lipid A (3-DMPL) is known from GB-A-2 220 211, corresponding to U.S. Pat. No. 4,912,094 and assigned to Ribi Immunochem. Res. ("Ribi"), now Corixa Corporation (Hamilton, Montana). Chemically, 3-DMPL is a mixture of 3 de-O-acylated monophosphoryl lipid A with 4, 5 or 6 acylated chains and is manufactured by Ribi Immunochem. Montana. A preferred form of 3 de-O-acylated monophosphoryl lipid A is disclosed in International Patent Publication No. WO 92/16556.

International Patent Publication No. WO 98/44947 describes a formulation for use in desensitization therapy of allergy sufferers that comprises an optionally modified allergen, tyrosine and 3 de-O-acylated monophosphoryl lipid A.

Considerable efforts have been made to produce better adjuvants, particularly for T-cell-mediated responses, but it should be stressed that very few of these more recent adjuvants have been accepted for routine human use.

It appears that the effect of adjuvants is due mainly to two activities: the concentration of antigen in a site where lymphocytes are exposed to it (the "depot" effect) and the induction of cytokines, which regulate lymphocyte function. Newer antigen delivery systems such as liposomes and immune-stimulating complexes (ISCOMS) achieve the same purpose by ensuring that antigens trapped in them are delivered to antigen-presenting cells. Bacterial products such as mycobacterial cell walls, endotoxins, etc., are believed to act by stimulating the formation of cytokines. Cytokine induction may be particularly useful in immunocompromised patients, who often fail to respond to normal vaccines. It is hoped that such cytokine induction might also be useful in directing the immune response in the desired direction, e.g., in diseases where only TH1 or TH2 cell responsiveness is wanted (Roitt et al "Immunology," 4th edition Wolfe Publishing, 1995).

We now provide a new antigen formulation that can tilt the TH1-TH2 balance in favor of a TH1 response. The formulation is useful in immunotherapy, particularly the field of vaccines. It is also useful in studying immune responses and in the production of antibodies.

SUMMARY OF THE INVENTION

According to one aspect of the present invention there is provided a composition comprising:
(a) an antigen;
(b) a TH1-inducing adjuvant; and
(c) a sparingly soluble amino acid or a derivative thereof.

Preferably, the antigen is derived from a bacterium or virus, or other pathogenic organism, or neoplasm or from knowledge of their antigenic structures.

Preferably, the TH1-inducing adjuvant is monophosphoryl lipid A (MPL),3'-de-O-acetylated monophosphoryl lipid A (3-DMPL), or a derivative or salt thereof.

Preferably, the sparingly soluble amino acid is tyrosine, tryptophan or a derivative thereof.

The present invention also provides a composition for use in medicine. That is, the invention provides a method for using a composition to treat or prevent or reduce susceptibility to a bacterial infection, a viral infection or other disease such as cancer.

Preferably, the composition is in the form of a vaccine, and the invention further provides a method for preparing an immunoglobulin, comprising immunizing an animal with a composition of the present invention.

The present invention also provides a method for preparing a composition of the present invention comprising mixing a solution of an antigen and the TH1-inducing adjuvant with a solution of the sparingly soluble amino acid or derivative in a strong aqueous acid while neutralizing the mixture of solutions, thereby co-precipitating the sparingly soluble amino acid, antigen and adjuvant. This method may further comprise adding a pharmaceutically acceptable carrier, diluent or excipient.

DETAILED DESCRIPTION OF THE INVENTION

I. The Antigen-Containing Formulation

The composition of the invention is an antigen-containing formulation comprised of an antigen, a $TH_1$-inducing adjuvant, and a sparingly soluble amino acid or a derivative thereof. The antigen-containing formulation is particularly useful as a vaccine; however, the formulation is useful in other contexts as well, e.g., in treating, preventing or reducing susceptibility to certain diseases and disorders, including, but not limited to, bacterial infections, viral infections, and cancer. The individual components of the formulation will now be described by way of non-limiting example.

(A) The Antigen

Originally the term "antigen" was used for any molecule that induced B cells to produce a specific antibody. Now, however, the term may be used to indicate any molecule that can be specifically recognized by the adaptive elements of the immune response, i.e., by B cells or T cells, or both. Thus, an "antigen" is a molecule that reacts with preformed antibody at specific receptors on T and B cells. However, we exclude what are traditionally known as "allergens," i.e., an agent, e.g., pollen dust, that causes IgE-mediated hypersensitivity.

An allergy is a response to an environmental antigen (allergen) due to pre-existing IgE antibody attached to mast cells. An immediate hypersensitivity reaction is produced by mast cell products (histamine, etc.) causing asthma, hay fever, serum sickness, systematic anaphylaxis or contact dermatitis. There are four types of such hypersensitivity reaction (Types I, II, III and IV). The first three are antibody-mediated; the fourth is mediated mainly by T cells and macrophages. The present invention does not relate to the use of such "environmental antigens."

Thus, preferably the "antigen" used in the present invention does not include an "allergen" derived from any allergy causing substance, such as pollen (e.g., ragweed or birch pollen), food, insect venom, mold, animal fur or house dust mite (*D. farinae* or *D. pteronyssinus*).

The present invention can therefore be seen as relating to antigens that often involve a cellular, IgG2a or IgG2b mediated response, rather than an IgE or IgG1 mediated response.

The antigen used in the present invention is preferably an immunogen, i.e., an antigen that activates immune cells to generate an immune response against itself.

In a preferred embodiment, the present invention relates to a formulation for use as a vaccine and the antigen is one that is useful in such a vaccine.

The antigen used in the present invention can be any appropriate antigen, which is or becomes available.

The type of antigen used in a vaccine depends on many factors. In general, the more antigens of the microbe retained in the vaccine the better, and living organisms tend to be more effective than killed ones. Exceptions to this rule are diseases where a toxin is responsible for any pathogenic effect. In this case the vaccine can be based on the toxin or toxoid alone.

The antigen used in the present invention may be derived from any living organisms; intact or non-living organisms; subcellular fragments; toxoids; recombinant DNA-based antigens or anti-idiotypes or synthetic antigens. The antigen may be derived from natural or attenuated organisms, which may be viral or bacterial. The type of antigen may be a capsular polysaccharide, surface or internal antigen. If recombinant DNA-based, the antigen may be obtained from a cloned and expressed gene or naked DNA.

The antigen may be modified by reaction, for example, with a cross-linking agent, such as a dialdehyde, more particularly glutaraldehyde.

For example, micro-organisms against which vaccines are available or are sought include Salmonella, Shigella, Klebsiella, Enterobacter, Serratia, Proteus, Yersinia, Vibrio, Aeromonas, Pasteurella, Pseudomonas, Acinetobacter, Moraxella, Flavobacterium, Bordetella, Actinobacillus, Neisseria, Brucella, Haemophilus and *Escherichia coli*.

Preferred vaccines include, but are not limited to: vaccinia (for smallpox); vole bacillus (for tuberculosis); polio; measles, mumps; rubella; yellow fever; varicella-zoster; BCG (Bacillus Calmette-Gruérin, an antituberculosis vaccine); rabies; influenza; hepatitis A; typhus; pertussis; typhoid; cholera; plague; pneumococcus; meningococcus; *Haemophilus influenzae*; hepatitis B; hepatitis C; tetanus and diphtheria. Toxin-based vaccines include *Clostridium tetani, Corynebacterium diphtheriae, Vibrio cholerae* and *Clostridium perfringens*.

Other major diseases for which the vaccines of the invention may be useful include, but are not limited to: HIV, herpes, viruses, adenoviruses, rhinoviruses, staphylococci, group A streptococci, Mycobacterium leprae, Treponema pallidum, Chlamydia, Candida, Pneumocystis, malaria, trypanosomiasis; Chagas' disease; schistosomiasis and onchoceriasis.

The presence of tumor antigens also has been demonstrated, and, as a result, the concept of vaccinating against cancer has arisen. Also, in principle, conception and implantation can be interrupted by inducing immunity against a wide range of pregnancy and other reproductive hormones.

(B) The Th1-Inducing Adjuvant

By "TH1-inducing adjuvant" is meant an adjuvant that enhances the TH1 response to an antigen.

The effectiveness of an adjuvant as a TH1-inducing adjuvant may be evaluated by determining the profile of antibodies directed against an antigen resulting from administration of this antigen in vaccines that are also comprised of the various adjuvants.

Preferably the adjuvant is a modified lipopolysaccharide. As described in U.S. Pat. No. 4,912,094, enterobacterial lipopolysaccharide (LPS) is a powerful immunostimulant. However, it can also elicit harmful and sometimes fatal responses. It is now known that the endotoxic activities associated with LPS result from its lipid A component. Accordingly, the present invention more preferably uses a detoxified derivative of lipid A. Ribi produced a derivative of lipid A originally known as refined detoxified endotoxin (RDE) but which has become known as monophosphoryl lipid A (MPL). As described in U.S. Pat. No. 4,912,094, MPL is produced by refluxing LPS or lipid A obtained from heptoseless mutants of gram negative bacteria (e.g., Salmonella sp.) in mineral acid solutions of moderate strength (e.g., 0.1N HCl) for a period of around 30 minutes. This treatment results in loss of the phosphate moiety at position 1 of the reducing-end glucosamine. In addition, the core carbohydrate is removed from the 6' position of the non-reducing glucosamine during this treatment.

Preferably, however, a modified LPS or lipid A is used in which the detoxified lipid A retains the core moiety attached to the 6' position of non-reducing glucosamine. Such derivatives of LPS and lipid A are also described in U.S. Pat. No. 4,912,094. In more detail, U.S. Pat. No. 4,912,094 discloses a modified lipopolysaccharide that is obtained by selectively removing only the β-hydroxymyristic acyl residue of lipopolysaccharide that is ester-linked to the reducing-end glucosamine at position 3' of said lipopolysaccharide, which comprises subjecting said lipopolysaccharide to alkaline hydrolysis. Such de-O-acylated monophosphoryl lipid A, diphosphoryl lipid A (DPL) and LPS may be used as the TH1-inducing adjuvant in the present invention. Thus in a preferred embodiment, the present invention uses MPL, DPL or LPS in which the position 3' of the reducing end glucosamine is de-O-acylated. These compounds are known as 3-DMPL, 3-DDPL and 3-DLPS respectively.

In U.S. Pat. No. 4,987,237 derivatives of MPL having the formula

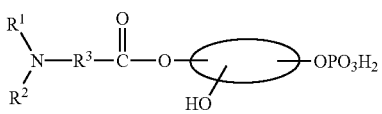

are described, wherein $R^1$ and $R^2$ are H or lower alkyl, and $R^3$ is straight or branched chain hydrocarbon composed of C, H and optionally O, N and S, which if more than one atom may be the same or different, wherein the total number of carbon atoms does not exceed 60, and the circle represents an MPL nucleus.

Alternatively, the MPL derivative has the formula

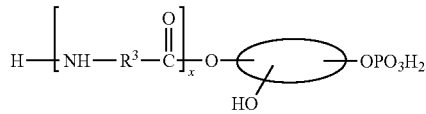

wherein the segment of the derivative represented by

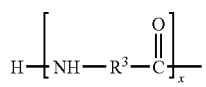

contains 2-60 carbon atoms and wherein $R^3$ is straight or branched chain hydrocarbon composed of C, H and optionally O, N and S, which if more than one atom may be the same or different, and x is a minimum of 1 and can be any whole number such that the total number of C atoms in all x segments does not exceed 60, and wherein the chemical structure of each $R^3$ may be the same or different in each such segment and wherein the circle represents an MPL nucleus.

All such derivatives of LPS or lipid A which are or become available may be used as the TH1-inducing adjuvants in the present invention.

The TH1-inducing adjuvant can be mixed with the other components of the composition prior to administration. Alternatively, it can be formulated together with the other components during manufacture of the product. Alternatively, it can be administered at a different site or time than the other components. Administration can be by a number of routes.

(C) The Sparingly Soluble Amino Acid

The amino acid of the present formulation must be sparingly soluble in aqueous solution such that the adjuvant and antigen are allowed to produce an immune response.

Most of the amino acids are only sparingly soluble in water, as a consequence of the strong intermolecular forces acting in the crystal lattice. Exceptions are glycine, proline, lysine, threonine, cysteine and arginine, which are all quite soluble in water, and do not form part of the invention. The water solubility of amino acids is given in the following Table:

| Amino Acid | Water Solubility g/100 ml $H_2O$ at 25° C. |
|---|---|
| glycine | 25 |
| alanine | 16.7 |
| valine | 8.9 |
| leucine | 2.4 |
| isoleucine | 4.1 |
| methionine | 3.4 |
| proline | 162 |
| phenylalanine | 3.0 |
| tryptophan | 1.1 |
| serine | 5.0 |
| threonine | very |
| cysteine | very |
| tyrosine | 0.04 |
| asparagine | 3.5 |
| glutamine | 3.7 |
| aspartic acid | 0.54 |
| glutamic acid | 0.86 |
| lysine | very |
| arginine | 15 |
| histidine | 4.2 |

Preferably the water solubility of the amino acid used in the invention is about 1.1 or less g/100 ml $H_2O$ at 25° C. Particularly preferred are tyrosine or tryptophan; the more insoluble tyrosine being preferred. Derivatives of these amino acids such as benzyl-O-octadecanoyl-L-tyrosine are also included within the scope of the present invention.

Typically, the antigen is dispersed within and/or adsorbed onto the amino acid, e.g., by co-precipitation or mixing, respectively.

II. Preparation

The composition of the present invention may be prepared by mixing an aqueous solution of the antigen with a solution of the amino acid in a strong aqueous acid, neutralizing the mixture of solution, thereby co-precipitating the amino acid and antigen, mixing the product with the TH1-inducing adjuvant, and optionally adding a physiologically acceptable diluent, excipient or carrier, before or after the aforementioned mixture. Alternatively, the TH1-inducing adjuvant may be co-precipitated with the antigen. As well as being mixed or co-precipitated with the other components of the composition prior to administration, the TH1-inducing adjuvant can be administered at a different site and/or time to the other components.

Typically an aqueous solution of the antigen, preferably at pH 7±1, obtainable from the solvation of a solid, is mixed with a solution of the amino acid in a strong aqueous acid. The strong acid is usually an inorganic acid, preferably hydrochloric acid. The solution of antigen used in this step typically contains between 0.1 μg/ml and 1000 μg/ml antigen protein, for example about 400 μg/ml. The ratio of antigen:amino acid in the mixture is typically in the range of approximately $1:4\times10^5$ to $1:1\times10^2$ w/w.

The resulting mixture of solutions of antigen and amino acid is neutralized. By neutralization is meant an adjustment of pH to a value within the range 4.0 to 7.5. It is desirable that, at no time, or at least no prolonged time, during the neutralization does the pH of the solution rise appreciably above 7.5. This condition can be met by vigorous stirring of the solution and by the use of only the required amount of base, if desired. Various buffering agents can usefully be added to the solutions of antigen to assist in pH control during mixing and neutralizing stages.

A particularly useful method of carrying out the neutralization is for separate streams of the solution of amino acid and neutralizing base to be run into the solution of antigen. The rates of flow of the added solutions are controlled by pH-stat, that is, by equipment that regulates the flow of one or both of the solutions so that the pH of the reaction mixture remains substantially constant at a predetermined level. Optimum results are generally obtained by maintaining the pH within the range of approximately 6.5 to 7.5, although the precise pH may vary according to the nature of the antigen.

The result of neutralization is the immediate precipitation of the amino acid, within and/or upon which the solution of antigen is occluded and/or adsorbed. After precipitation, the mixture is either washed immediately or allowed to stand for a period of from a few hours to a day or two prior to washing.

The resulting precipitate may be removed from the solution by centrifugation or filtration and washed, e.g., with phenol-saline, before resuspending, if required, in a physiologically acceptable carrier, excipient or diluent.

MPL (or other TH1-inducing adjuvant) that has been dissolved by the method described in Preparation 3 below or by sonification can be diluted by various means prior to its addition to amino acid adsorbates of antigens. The preparation of MPL is initially made at a concentration of typically between 0.5 mg per ml and 4 mg per ml, for example 1 mg per ml. It can then be diluted to a concentration of between 500 µg/ml and 20 µg/ml, preferably 100 µg/ml. This dilution can be made in pure water, or in an aqueous glycerol solution containing between 1% and 4%, preferably 2%, glycerol. Such dilutions can then be added to a suspension of the amino acid adsorbate prepared as described above. For convenience, the concentration of the MPL solution and the amino acid adsorbate suspension respectively may be selected such that approximately equal volumes of each of admixed to obtain the final product for injection. A typical final product contains about 100 µg/ml of antigen and about 250 µg/ml of MPL.

Thus, although the formulation of the invention may be administered directly, preferably the formulation is combined with a pharmaceutically acceptable carrier, excipient or diluent to produce a pharmaceutical composition, which may be for human or veterinary use. Suitable physiologically acceptable carriers and diluents include isotonic saline solutions, for example phosphate-buffered saline, phenol-saline and sterile water. The compositions may be formulated for parenteral, intramuscular, intravenous, subcutaneous, intraocular or transdermal administration.

The routes of administration and dosages described herein are intended only as a guide since a skilled practitioner will readily be able to determine the optimum route of administration and dosage for any particular patient and condition.

III. Vaccines

Vaccines may be prepared from the formulation of the present invention. The preparation of vaccines that contain an antigen as active ingredient is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the formulation encapsulated in liposomes. As indicated above, the formulation may be mixed with carriers, diluents and excipients that are pharmaceutically acceptable and compatible with the formulation. Such excipients include, for example, water, saline, dextrose, glycerol, ethanol, or the like and combinations thereof.

In addition, if desired, the vaccine may contain minor amounts of auxiliary substances such as wetting or emulsifying agents, pH buffering agents and/or further adjuvants that enhance the effectiveness of the vaccine.

The proportion of antigen and adjuvant can be varied over a broad range so long as both are present in effective amounts. Conveniently, the vaccines are formulated to contain a final concentration of antigen in the range of 0.2 µg/ml to 200 µg/ml, preferably 5 µg/ml to 50 µg/ml, most preferably about 15 µg/ml.

After formulation, the vaccine may be incorporated into a sterile container that is then sealed and stored at low temperature, for example 4° C., or it may be freeze-dried. Lyophilization permits long-term storage in a stabilized form.

The vaccines are conventionally administered parenterally, by injection, for example, either subcutaneously or intramuscularly. Additional formulations that are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1% to 2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the vaccine composition is lyophilized, the lyophilized material may be reconstituted prior to administration, e.g., as a suspension. Reconstitution is preferably effected in buffer.

Capsules, tablets and pills for oral administration to a patient may be provided with an enteric coating comprising, for example, copolymers of methacrylic acid and methyl methacrylate available under the trademark Eudragit S, and Eudragit L, cellulose acetate, cellulose acetate phthalate or hydroxypropylmethyl cellulose.

The antigens used in the invention may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or organic acids such as acetic, oxalic, tartaric and maleic. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine and procaine.

IV. Dosage and Administration of Vaccines

The vaccines are administered in a manner compatible with the dosage formulation, and in such amount as will be prophylactically and/or therapeutically effective. The quantity to be administered, which is generally in the range of 5 µg to 250 µg of antigen per dose, depends on the subject to be treated, capacity of the subject's immune system to synthesize antibodies, and the degree of protection desired. A preferable range is from about 20 μg to about 40 μg per dose.

A suitable dose size is about 0.5 ml. Accordingly, a dose for intramuscular injection, for example, would comprise 0.5 ml containing 20 μg of immunogen in admixture with 0.5% adjuvant.

Precise amounts of active ingredient required to be administered will depend on the judgment of the practitioner and may vary with each subject.

The vaccine may be given in a single dose schedule, or preferably in a multiple dose schedule. A multiple dose schedule is one in which a primary course of vaccination may be with 1-10 separate doses, followed by other doses given at subsequent time intervals required to maintain and or reinforce the immune response, for example, at 1 to 4 months for a second dose, and if needed, a subsequent dose(s) after several months. The dosage regimen will also, at least in part, be determined by the need of the individual and be dependent upon the judgement of the practitioner.

In addition, the vaccine containing the antigen(s) may be administered in conjunction with other immunoregulatory agents, for example, immunoglobulins.

V. Preparation of Antibodies Using the Formulation of the Invention

Compositions according to the invention may be used directly as immunogens, without the use of further adjuvants to generate antisera and monoclonal antibodies. The invention thus provides a method for inducing antigen specific immunoglobulin production comprising the steps of:
a) immunizing an animal with a composition according to the present invention; and
b) recovering immunoglobulin specific for a region of the antigen of the composition from the serum of the animal.

The animals used for antibody production may be any animals normally employed for the purpose, particularly mammals. Especially indicated are mice, rats, guinea pigs and rabbits.

Immunization is carried out according to established techniques (See "Antibodies, A Laboratory Manual" by E. Harlow and D. Lane (1988) Cold Spring Harbor, U.S.A.). The purified composition (about 1 mg) was injected into a rabbit. A booster injection of 0.5 mg of the composition was made 4 weeks after the initial injection. Antibodies are isolated from rabbit serum and tested for reactivity. Antibodies capable of selective binding to the chosen antigen are obtained by this method.

More particularly, the formulation of the present invention comprising the antigen can be used to produce antibodies, both polyclonal and monoclonal. If polyclonal antibodies are desired, a selected mammal (e.g., mouse, rabbit, goat, horse, etc.) is immunized. Serum from the immunized animal is collected and treated according to known procedures. If serum containing polyclonal antibodies to other antigens, the polyclonal antibodies can be purified by immunoaffinity chromatography. Techniques for producing and processing polyclonal antisera are known in the art.

Monoclonal antibodies directed against antigens used in the invention can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against antigens can be screened for various properties; i.e., for isotype and epitope affinity.

An alternative technique involves screening phage display libraries where, for example, the phage express scFv fragments on the surface of their coat with a large variety of complementary determining regions (CDRs). This technique is well known in the art.

Antibodies, both monoclonal and polyclonal, which are directed against antigens are particularly useful in diagnosis, and those which are neutralizing are useful in passive immunotherapy. Monoclonal antibodies, in particular, may be used to raise anti-idiotype antibodies. Anti-idiotype antibodies are immunoglobulins that carry an "internal image" of the antigen of the infectious agent against which protection is desired.

Techniques for raising anti-idiotype antibodies are known in the art. These anti-idiotype antibodies may also be useful for treatment, as well as for an elucidation of the immunogenic regions of antigens.

For the purposes of this invention, the term "antibody," unless specified to the contrary, includes fragments of whole antibodies that retain their binding activity for a target antigen. Such fragments include Fv, F(ab') and F(ab')2 fragments, as well as single chain antibodies (scFv). Furthermore, the antibodies and fragments thereof may be humanized antibodies, for example as described in EP-A-239400.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

All patents, patent applications, and publications mentioned herein, both supra and infra, are hereby incorporated by reference.

REFERENCE EXAMPLE

Preparation 1:

Eight mg of ovalbumin (XOA) as a model allergen were dissolved by mixing in 20 ml of EVANS solution, a standard physiological buffered saline solution. Next, 6.9 ml of phosphate buffer was added with mixing. The solution was placed in a 100 ml beaker containing a magnetic stir bar. While mixing using a magnetic stirrer, 6.9 ml or 3.2N NaOH and 6.9 ml of 3.8N HCl, containing 24% w/v tyrosine were added simultaneously, dropwise, over a period of 5 minutes to form a precipitate. The mixture was allowed to stir for an additional 5 minutes and then transferred to a 50 ml centrifuge tube and centrifuged for 10 minutes at 2500 rpm. After centrifugation the supernatant was decanted and the pelleted precipitate resuspended in 40 ml of phosphate buffer. The mixture was centrifuged for 5 minutes at 2500 rpm. After centrifugation the supernatant was decanted and the precipitate resuspended in 40 ml of phosphate buffer. The mixture was centrifuged for 5 minutes at 2500 rpm. After centrifugation the supernatant was decanted and the pelleted precipitate resuspended in 40 ml of phosphate buffer saline, pH 7.2 containing 0.4% v/v glycerol and 0.01% w/v thimerosal as a preservative. The final product contained approximately 40 mg/ml of tyrosine adsorbate. Assuming 100% binding of the XOA to the tyrosine adsorbate the XOA was at 200 μg/ml in the final product. The XOA tyrosine adsorbate was stored at 4° C. until needed.

Preparation 2:

A 4 mg/ml solution of 1.2-dipalmitoyl-SN-glycero-3-phospho choline (DPPC) in absolute ethanol was prepared. For each 1.0 mg of MPL®-TEA (triethylamine) salt to be solubilized, 27 µl of DPPC were added to dissolve the MPL®. The ethanol was removed by blowing a stream of $N_2$ gently into the vial. Next 1.0 ml of pyrogen-free water for injection was added for each mg of MPL® in the dried MPL®/DPPC mixture. The solution was sonicated in a bath sonicator at 60-70° C. until clear. The MPL®/DPPC solution was then filter sterilized by filtration through a SFCA 290-4520 Nalgene 0.2 µm filter. The MPL®/DPPC solution was aseptically dispensed at 1.0 mg/ml into depyrogenated vials, labelled MPL®-AF, and stored at 4° C.

Biological Activity:

TH1 inducing activity in mice can be equated with the production of IgG2a and IgG2b antibodies and the TH2 inducing activity with the production of IgG1 antibodies and IgE antibodies.

Therefore, as an example, an experiment was carried out in mice to demonstrate the profiles of the allergen specific antibodies to an exemplar ovalbumin (XOA) which is a well-known allergen derived from chicken eggs. It was confirmed that a formulation consisting of MPL+XOA+tyrosine stimulated a more advantageous antibody profile than MPL+XOA, XOA+tyrosine or XOA alone.

Groups of 8 BALB/c female mice, 6-8 weeks of age, were injected subcutaneously in the inguinal area with 0.2 ml of one of the following vaccines.

XOA+Tyrosine:

The XOA tyrosine adsorbate prepared in Preparation 1 above was diluted with an equal volume of phosphate buffered saline within 30 minutes prior to injection.

XOA+Tyrosine+MPL:

The XOA tyrosine adsorbate prepared in Preparation 1 above was diluted with an equal volume of MPL®-AF at 500 µg/ml in phosphate buffered saline within 30 minutes prior to injection.

XOA+MPL:

XOA was dissolved in phosphate buffered saline at 200 µg/ml and diluted with an equal volume of MPL®-AF at 500 µg/ml in phosphate buffered saline within 30 minutes prior to injection.

XOA Alone:

XOA was dissolved at 200 µg/ml in phosphate buffered saline and diluted with an equal volume of phosphate buffered saline.

Twenty-one days later the four groups of mice were boosted with 0.2 ml of freshly prepared vaccines. Fourteen days following the booster the mice were bled and the sera separated and stored at −70° C. until assay.

The sera were assayed by conventional ELISA technique using horseradish conjugated goat anti-mouse $IgG_1$, $IgG_{2a}$ and $IgG_{2b}$ antibodies purchased from Southern Biotechnology Inc. (Birmingham, Ala.) and used according to the manufacturer's instruction. The IgG1, IgG2a and IgG2b titers represent the reciprocal serum dilution giving a reading of >0.1 OD units at $A_{490}$.

The serum IgE levels were measured using an anti-IgE capture ELISA followed by the use of a biotinylated ovalbumin probe. Binding was measured following the addition of a horseradish conjugated strepavidin preparation. The results are reported as OD units at $A_{490}$.

Results:

Of particular importance is the fact that the combination of allergen+tyrosine+MPL induces less antigen specific IgE antibody than the other combinations. Furthermore, the ratio of IgG2a or IgG2b to IgG1 antibodies is greater and consistent with the highest levels of the two former antibody isotypes seen in the experiment in the mice given antigen+tyrosine+MPL than in any other group of mice. This is indicative of a better ratio of TH1 cell induction over TH2 cell induction in this group compared with that induced in the other groups of mice.

EXAMPLES ACCORDING TO THE PRESENT INVENTION

Preparation A:

To a neutral solution of purified polypeptide that displays hepatitis B virus antigenicity (details of how to prepare such a polypeptide can be found in EP-A-0 182 442 and WO 98/44947) is added phosphate buffer solution at a pH of 7±1. The antigen solution is co-precipitated with tyrosine by the simultaneous addition of one volume of L-tyrosine in HCl (prepared by dissolving 24 g L-tyrosine to 100 ml with 3.8M HCl) and one volume of 3.2M NaOH, to four volumes of antigen solution, with vigorous agitation. The suspension so formed is centrifuged and then washed repeatedly with buffered saline pH 6±1.

Preparation B:

As for Preparation 1 of Reference Example, except that XOA is replaced with a polypeptide that displays hepatitis virus (HBV) antigenicity.

Preparation C:

Same as Preparation 2 of Reference Example.

Biological Activity:

TH1 inducing activity in mice can be equated with the production of IgG2a and IgG2b antibodies and the TH2 inducing activity with the production of IgG1 antibodies and IgE antibodies.

Therefore, as an example, an experiment is carried out in mice to demonstrate the profiles of the antigen specific antibodies to an exemplar antigen (HBV) which is a well-known antigen. It is confirmed that a formulation consisting of MPL+HBV+tyrosine stimulates a more advantageous antibody profile than MPL+HBV, HBV+tyrosine or HBV alone.

Groups of 8 BALB/c female mice, 6-8 weeks of age, are injected subcutaneously in the inguinal area with 0.2 ml of one of the following vaccines.

HBV+Tyrosine:

The HBV tyrosine adsorbate prepared in Preparation A above is diluted with an equal volume of phosphate buffered saline within 30 minutes prior to injection.

HBV+Tyrosine+MPL:

The HBV tyrosine adsorbate prepared in Preparation A above is diluted with an equal volume of MPL®-AF at 500 µg/ml in phosphate buffered saline within 30 minutes prior to injection.

HBV+MPL:

HBV is dissolved in phosphate buffered saline at 200 µg/ml and diluted with an equal volume of MPL®-AF at 500 µg/ml in phosphate buffered saline within 30 minutes prior to injection.

HBV Alone:

HBV is dissolved at 200 μg/ml in phosphate buffered saline and diluted with an equal volume of phosphate buffered saline.

Twenty one days later the four groups of mice are boosted with 0.2 ml of freshly prepared vaccines. Fourteen days following the booster the mice are bled and the sera separated and stored at −70° C. until assay. The sera are assayed by conventional ELISA technique using horseradish conjugated goat anti-mouse $IgG_1$, $IgG_2a$ and $IgG_2b$ antibodies purchased from Southern Biotechnology Inc. (Birmingham, Ala., U.S.A.) and used according to the manufacturer's instructions. The $IgG_1$, $IgG_{2a}$ and $IgG_{2b}$ titers represent the reciprocal serum dilution giving a reading of >0.1 OD units at $A_{490}$. The serum IgE levels are measured using an anti-IgE capture ELISA followed by the use of a biotinylated ovalbumin probe. Binding is measured following the addition of a horseradish conjugated strepavidin preparation. Of particular importance is the fact that the combination of antigen+tyrosine+MPL may induce less antigen specific IgE antibody than the other combinations. Furthermore, the ratio of IgG2a or IgG2b to IgG1 antibodies may be greater and consistent with the highest levels of the two former antibody isotypes seen in the experiment in the mice given antigen+tyrosine+MPL than in any other group of mice. This is indicative of a better ratio of TH1 cell introduction over TH2 cell induction in this group compared with that induced in other groups of mice.

The invention claimed is:

1. A method of preparing an antigen-containing formulation, comprising the steps of:
    (a) mixing an aqueous solution of antigen with a solution of amino acid in a strong aqueous acid, wherein the amino acid is selected from the group consisting of tyrosine, benzyl-O-octadecanoyl L-tyrosine, and tryptophan;
    (b) neutralizing the solution of step (a) to co-precipitate the amino acid and antigen;
    (c) resuspending the co-precipitate of step (b) in buffer; and
    (d) mixing the solution of step (c) with a TH1-inducing adjuvant, wherein the TH1-inducing adjuvant is selected from the group consisting of monophosphoryl lipid (MPL), 3-de-O-acylated monophosphoryl lipid (3-DMPL), lipopolysaccharide (LPS), 3-de-O-acylated lipopolysaccharide (3-DLPS), diphosphoryl lipid A (DPL), and 3-de-O-acylated diphosphoryl lipid A (3-DDPL).

2. The method of claim 1, further comprising adding a pharmaceutically acceptable carrier, diluent, or excipient to the mixture.

3. The method of claim 1, wherein the antigen is derived from a bacterium, virus, or neoplasm.

4. The method of claim 1, wherein the antigen comprises a polypeptide.

5. The method of claim 3, wherein the antigen comprises a polypeptide.

6. The method of claim 2, wherein the antigen containing formulation is a vaccine.

7. A method for preparing an antigen-containing formulation, comprising:
    (a) mixing an aqueous solution of an antigen with a solution of an amino acid in a strong aqueous acid while neutralizing the mixture of solutions, thereby co-precipitating the amino acid and antigen, wherein the amino acid is selected from the group consisting of tyrosine, benzyl-O-octadecanoyl L-tyrosine, and tryptophan; and
    (b) mixing the precipitate with a TH1-inducing adjuvant selected from the group consisting of monophosphoryl lipid (MPL), 3-de-O-acylated monophosphoryl lipid (3-DMPL), lipopolysaccharide (LPS), 3-de-O-acylated lipopolysaccharide (3-DLPS), diphosphoryl lipid A (DPL), 3-de-O-acylated diphosphoryl lipid A (3-DDPL).

8. The method of claim 1 or 7, wherein during neutralization of the mixture of solutions, pH of the mixture of solutions remains at a neutral pH.

9. The method of claim 7, wherein the amino acid and the neutralizing base are added simultaneously to the antigen solution.

10. The method of claim 7, wherein the precipitate is washed prior to mixing with the TH1-inducing adjuvant.

11. The method of claim 7, wherein the antigen is derived from a bacterium, virus, or neoplasm.

12. The method of claim 7, wherein the antigen comprises a polypeptide.

13. The method of claim 11, wherein the antigen comprises a polypeptide.

14. The method of claim 7, further comprising adding a pharmaceutically acceptable carrier, diluent, or excipient to the mixture.

15. The method of claim 14, wherein the antigen containing formulation is a vaccine.

* * * * *

UNITED STATES PATENT AND TRADEMARK OFFICE
CERTIFICATE OF CORRECTION

| | | |
|---|---|---|
| PATENT NO. | : 7,815,920 B2 | Page 1 of 1 |
| APPLICATION NO. | : 10/211388 | |
| DATED | : October 19, 2010 | |
| INVENTOR(S) | : Alan Wheeler and Antony Berry | |

It is certified that error appears in the above-identified patent and that said Letters Patent is hereby corrected as shown below:

ON THE TITLE PAGE:

Item (75) Inventors: Inventor Berry's given name should be replaced with --Antony--.

Signed and Sealed this

Twenty-first Day of December, 2010

David J. Kappos
*Director of the United States Patent and Trademark Office*